United States Patent [19]

Hull, Jr. et al.

[11] 4,170,305

[45] Oct. 9, 1979

[54] EASY-OPEN WRAPPER FOR CYLINDRICAL PRODUCTS

[75] Inventors: Raymond J. Hull, Jr., Maplewood; William F. Hoppes, Somerset, both of N.J.

[73] Assignee: Johnson & Johnson, New Brunswick, N.J.

[21] Appl. No.: 932,966

[22] Filed: Aug. 11, 1978

[51] Int. Cl.² ............................................. B65D 3/26
[52] U.S. Cl. .................................... 206/606; 206/611
[58] Field of Search .............. 206/264, 438, 602, 604, 206/605, 606, 608, 610, 611, 612, 623, 627; 229/87 R, 87 C

[56] References Cited

U.S. PATENT DOCUMENTS

| | | | |
|---|---|---|---|
| 2,285,542 | 6/1942 | Tasker | 206/606 |
| 2,679,349 | 5/1954 | Mullinix | 206/606 X |
| 3,620,438 | 11/1971 | Wood | 206/611 X |
| 3,856,143 | 12/1974 | Simon | 206/438 |

*Primary Examiner*—Donald F. Norton
*Attorney, Agent, or Firm*—Jason Lipow

[57] ABSTRACT

A wrapped cylindrical body such as a catamenial tampon is provided with a wrapper which will maintain the body clean and dust and moisture proof and can easily be opened. Specifically, the cylindrical body is wrapped in a wrapper having perforations arranged in a pattern whereby almost the entire wrapper can be removed in one motion without the need for pulling substantial quantities of wrapping from the ends of the cylindrical body. Further, the wrapper provides no open path for dust and other contaminants to reach the wrapped product. These advantages are achieved by providing two perforated zones in the wrapping material, double wrapping the cylindrical body and having the perforations of each of the zones offset so as to close any path into the product. The zones are located so as to overlie each other when the product is wrapped and are adhered together whereby essentially the entire product may be unwrapped in a single unwrapping operation.

16 Claims, 6 Drawing Figures

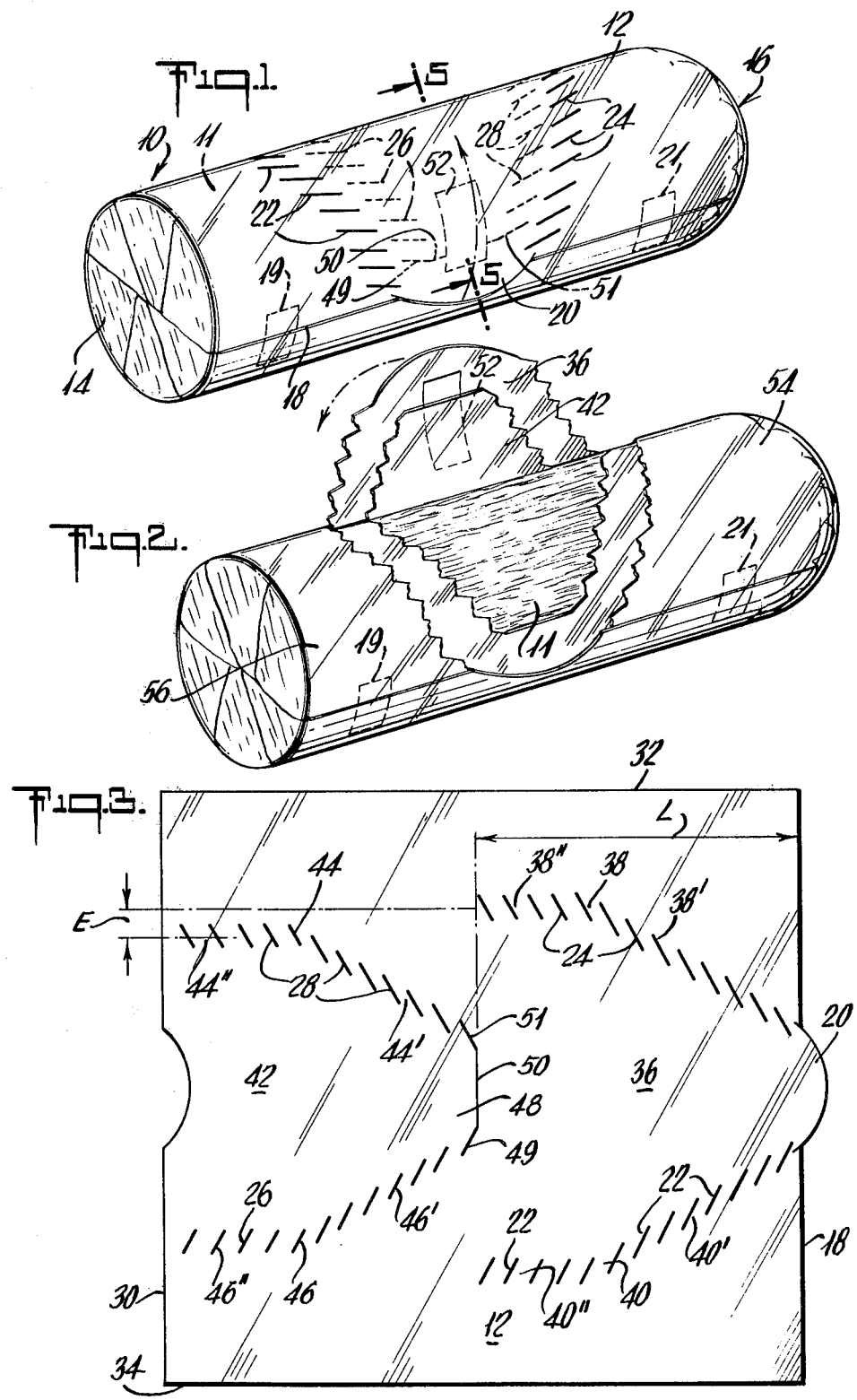

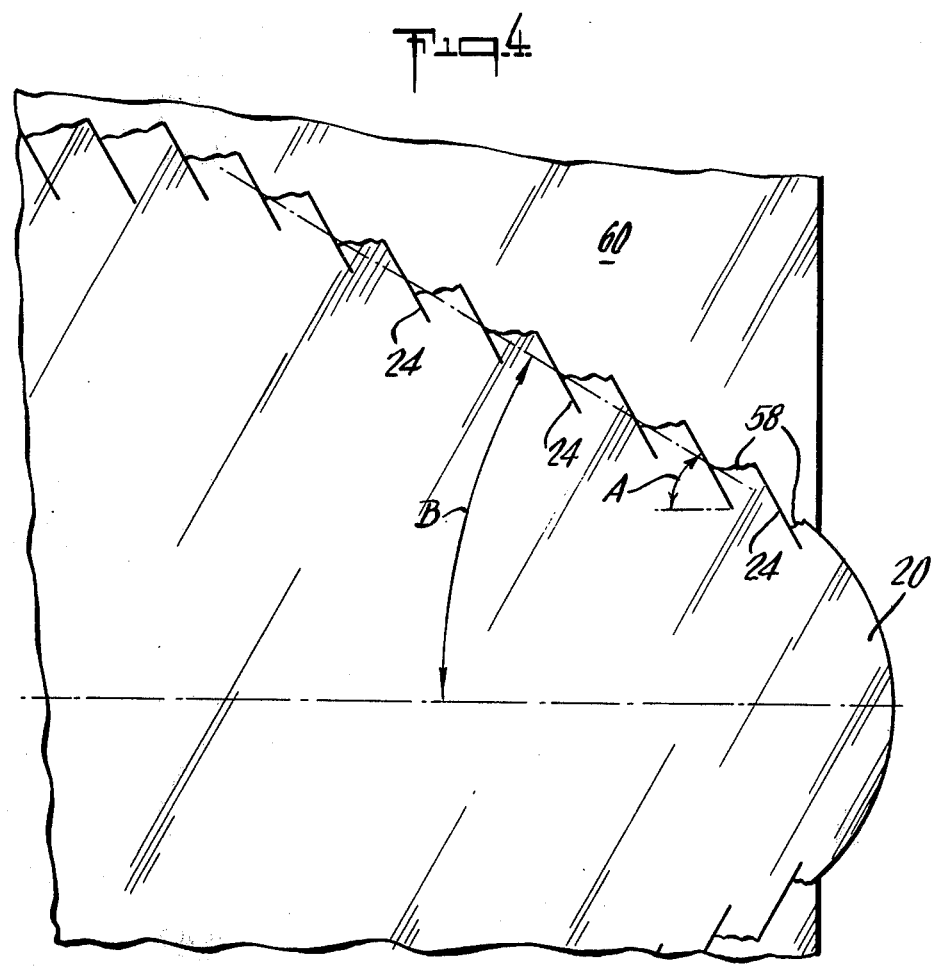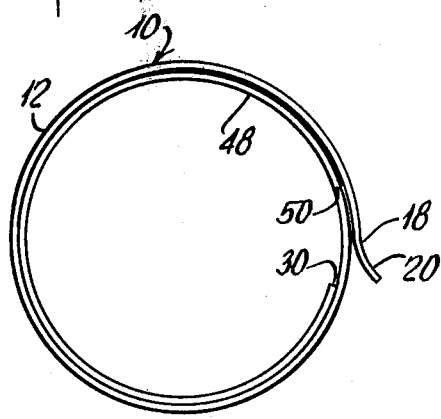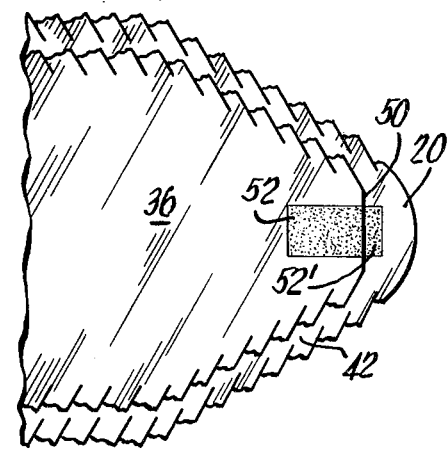

EASY-OPEN WRAPPER FOR CYLINDRICAL PRODUCTS

BACKGROUND OF THE INVENTION

This invention concerns wrappers for cylindrical bodies and in particular concerns wrappers for products which can be easily opened but at the same time should be protected from dirt, dust, moisture or other contamination while wrapped such as, for example, catamenial tampons. While the invention will be discussed specifically in terms of catamenial tampons, it will be understood that the problems toward which this invention is directed and their solution applies to many similar products, including, for example, foods, tobacco products and the like.

Catamenial tampons, and particularly those which are meant to be inserted digitally as contrasted with applicator insertion, have employed tight wrappers in which each tampon is heat sealed within a tubular sleeve of wrapping material. The wrapping serves two functions. Firstly, it prevents dirt or other foreign material from contaminating the tampon prior to use. Secondly, because these tampons of necessity comprise highly absorbent material, they tend to pick up ambient moisture and deform. The tight wrapping aids in maintaining the shape of the tampon and preventing such deformation. A tampon of the kind being described herein and a method for wrapping the same is described in U.S. Pat. No. 3,856,143, issued on Dec. 24, 1974 to Stefan Simon et al.

Unfortunately, such wrappers as those described in the above-mentioned patent, while being highly effective in accomplishing the purpose of maintaining the tampons hygienically pure and deformation free, suffer from the drawback of being difficult to open when the tampon is to be used. Frequently, such tampons are provided with a tearstrip at a point about midway along the axial length of the tampon. This tearstrip generally comprises a narrow band of supportive material adhered all along the inside periphery of the wrapped tampon and ends in a tab, notched on either side. The tab is lifted and pulled and, because of the notching, tears begin to propagate in the direction of the pull. Such tears tend to neck in together toward the center of the wrapper and so will continue to do so until stopped by the supportive material. Thereafter the tears will propagate along each side of the supportive material and completely around the tampon until a narrow band of wrapper is completely removed, effectively cutting the wrapper in half. The two ends of remaining wrapper material are then removed by pulling them from the center and towards the ends of the tampon.

Unfortunately, this method of wrapping has encountered difficulties. Because the tampon is so tightly wrapped and because of the high frictional forces existing between the tampon and the inside surface of the remaining end pieces of the wrapper, it is extremely difficult to remove those end pieces. This situation is aggravated when the tampon is in a humid environment, as when stored in a bathroom or shower room. Under these circumstances, the tampon tends to swell and make the fit of the wrapper even tighter hence increasing the frictional forces resisting wrapper removal. Additionally, the outer surface of the wrapper may be moist, thus making it even more difficult to grip.

For the aforementioned reasons, there is a need for an improved tampon wrapper. Specifically, a wrapper is needed which will allow a greater portion to be removed thus leaving only a minimal amount of wrapper material on the ends of the tampon. To remove such a greater amount of material necessitates an alternative means to that of the tearstrip method described above and further requires that the wrapper material be weakened, as by means of perforations, to have the wrapper tear in a controlled manner. Unfortunately, perforations in the wrapper generally means that a flow path for dirt and contamination is created which is, of course, highly undesirable. Accordingly, a wrapper must be provided which can easily be unwrapped from the product and will not expose the product to contamination.

SUMMARY OF THE INVENTION

In accordance with this invention, a wrapped cylindrical body is provided which overcomes the disadvantages of prior wrapping methods and presents a wrapped product which is tightly wrapped, clean and dust proof and can easily be opened.

In particular, this invention provides a wrapper having perforation for easy opening and arranged in a pattern which defines perforated zones encompassing the major portion of the wrapping so that the user, when opening the wrapper will remove almost the entire wrapper in one motion without the need to pull substantial quantities of wrapping from the ends of the cylinder. Notwithstanding the fact that the perforations are cut entirely through the wrapping material, by utilizing the teachings of this invention, no open path is available for dust to reach the wrapped product.

This important advantage is achieved by providing two perforated zones in the wrapping material, double wrapping the cylindrical body and having the perforations of each of the zones off set so as to close any path into the product. By properly locating the perforated zones with respect to one another and by adhering them together, the perforations of both zones may be broken and essentially the entire product may be unwrapped in a single unwrapping operation.

Specifically, this invention contemplates a cylindrical body wrapped in a protective tearable wrapper having a generally rectangular shape with first and second transverse edges of a width equal to at least the length of the cylindrical body and first and second longitudinal edges of a length equal to at least twice the radial circumference of the body. Preferably, the transverse edges are wider than the length of the body to provide means for sealing the ends of the wrapped body, as described herein. The wrapper is provided with a first pattern of perforations, consisting of slits cut into the wrapper material and defining a first perforated zone. This first pattern of perforations consists of two legs, each of which begin at the first transverse edge of the wrapper and extend generally toward and along to each of the longitudinal edges of the wrapper.

A second pattern of perforations defining a second perforated zone is provided and also consists of two legs. In this case each of the legs begin at a longitudinal distance from the first transverse edge of the wrapper equal to at least one circumference of the cylindrical body. This set of legs then extends generally parallel to each of the legs of the first pattern but is displaced inwardly (with respect to the longitudinal edges of the wrapper) of the legs of the first pattern.

The wrapper is rolled about the cylindrical body with the transverse edges of the wrapper being aligned parallel to the axis of the body. In the wrapped position the first perforated zone overlies the second perforated zone and is adhered thereto at the first transverse edge of the wrapper. Because the legs of the perforation pattern of the second zone are displaced inwardly of the legs of the first zone, the individual perforations are misaligned and thereby prevent an open path to the cylindrical body precluding the entry of dirt or other contaminants.

The cylindrical body may be unwrapped simply by gripping the first transverse edge and pulling the wrapper so as to break the perforations. The perforations of both zones will break together and the entire wrapper can be removed at once with the possible exception of only minor amounts of wrapper remaining at the ends of the cylindrical body. Preferably, not even minor amounts remain. In any event, those minor amounts which do remain can easily be removed by pulling them off of the body because the area of contact with the body is so small that no significant frictional resistance to removal is generated.

In a preferred embodiment of the invention, each of the legs of the perforated patterns is broken into two parts; one parallel to the edges of the wrapper and a second connecting the parallel portion and running at an angle toward the center of the wrapper. The pattern therefore takes the shape of a chevron and this shape facilitates the propagation of the tear from perforation to perforation.

BRIEF DESCRIPTION OF THE DRAWINGS

In the drawings:

FIG. 1 is a perspective view of a fully wrapped catamenial tampon embodying the teachings of this invention;

FIG. 2 is a perspective view of the wrapped tampon of FIG. 1 with the wrapper partially removed;

FIG. 3 is a planar view of the wrapper of this invention illustrating the pattern of perforations;

FIG. 4 is an enlarged view of a portion of the wrapper of FIG. 3 illustrating the propagation of the tears as the wrapper is removed from the tampon;

FIG. 5 is a radial cross-sectional view of the wrapped tampon of FIG. 1 taken through line 5—5; and FIG. 6 is a view of a portion of the wrapper of FIG. 2.

DETAILED DESCRIPTION OF THE INVENTION

Referring now to the drawings, illustrated in FIG. 1 is a wrapped cylindrical body 10 of this invention and specifically a catamenial tampon 11. The tampon 11 is wrapped in a flexible, tearable, generally moisture and vapor resistant material for the purpose of cleanliness and also to preserve its shape. The wrapper 12 may be chosen from a wide variety of commonly used wrapper materials such as polymeric films or metal foils or even treated papers. The material of choice in connection with this invention is cellophane which advantageously combines the desired strength, flexibility and tearability properties. Preferably, the cellophane has been treated such as by coating with a suitable material so as to be readily heat sealable. The wrapper 12 is rolled about the cylindrical tampon and the ends 14 and 16 are sealed closed by means of heat sealing, by the use of adhesives or by simply twisting, folding or crimping closed. The transverse edge 18 is sealed closed, preferably by heat sealing, at seal points 19, 21 and 52. The wrapper is to be removed from the tampon by pulling up tab 20 located in the transverse edge 18 of the wrapper and then breaking the perforations 22, 24, 26 and 28 to tear the wrapper and free the tampon. In accordance with the teachings of this invention, the unique configuration of the perforations coupled with the other features of this invention allow the wrapper to be easily removed from the tampon leaving only a minimal quantity of wrapping material remaining on the ends 14 and 16 of the product.

The invention can be best understood by referring to FIG. 3 which illustrates, in planar view, the wrapper 12 and its pattern of perforations. The wrapper is a generally rectangular sheet of material such as those described above and preferably cellophane, having first and second transverse edges 18 and 30, respectively, each of which is at least as long as the axial length of the tampon to be wrapped. The longitudinal edges 32 and 34 are each at least twice as long as the circumference of the tampon.

The wrapper 12 is provided with a pattern of perforations defining a first perforated zone 36 bordered by perforations 24 and 22 arranged in two legs 38 and 40 each of which extend from the first transverse edge 18 toward the second transverse edge 30 and toward and along longitudinal edges 32 and 34, respectively. Perforations 24 and 22 are slits cut into the sheet of the wrapper and set out an angle for reasons which will be clearer from a further description of this invention. Preferably legs 38 and 40 are each divided into two portions; 38' and 38", 40' and 40". Portions 38" and 40" are generally parallel to their respective longitudinal edges 32 and 34 and portions 38' and 40' connect these parallel portions to the approximate center of the first transverse edge 18 so that this first pattern of perforations is in the general shape of a chevron whose apex lies on the transverse edge 18. It has been discovered that this chevron shape is best suited for propagating a tear along the desired path without having the wrapper tear in an uncontrolled manner. The transverse edge 18 is provided with a tab 20 for gripping the wrapper and initiating the tear.

The wrapper 12 is provided with a second perforated zone 42 bordered by perforations 26 and 28 and arranged in two legs 44 and 46 each of which extend from a point at a longitudinal distance from the first transverse edge 18 equal to the dimension L shown on the drawing. The dimension L is equal in length to at least one full circumference of the tampon being wrapped. Again, legs 44 and 46 are divided into two portions 44' and 44" and 46' and 46" to form a chevron pattern with portions 44" and 46" being parallel to longitudinal edges 32 and 34 respectively. Portions 44' and 46' connect the parallel portion to the apex area 48 (i.e., that area of the chevron pattern adjacent to its apex) which is defined by perforations 49, 50, 51. It is important to note that parallel portions 44" and 46" of the second chevron pattern are offset from the corresponding parallel portions of the first perforation pattern (38" and 40", respectively) by a distance, shown in the drawing by the dimension E. This offset is provided to insure that when the wrapper is rolled about the tampon, the perforations will be misaligned and thus provide no open path for dust or other contaminants. Preferably the distance E is equal to at least 0.643 times the length of a perforation and less than 1.93 times the length.

Referring now to FIGS. 1 and 5, the wrapper 12 is rolled about the tampon starting the second edge 30 parallel to longitudinal axis of the tampon and ending with first edge 18, also parallel to the longitudinal axis of the tampon and now on the external surface of the wrapped tampon so that tab 20 is accessible. The wrapper is held closed by heat seals 19, 21 and 52 and the ends 14 and 16 are also heat sealed. It will be noted that in the wrapped state, the wrapper effectively double wraps the tampon with the first perforated zone 36 overlying the second perforated zone 42 and the perforations forming the first zone lying outside and offset from (with respect to the longitudinal edge of the wrapper) the perforation of the second zone. Accordingly, no direct path for contaminants is available.

The first transverse edge 18 which includes the apex of the first perforated zone 36 also overlies the apex area 48 of the second perforated zone 42. In accordance with this invention, the apex areas of the two zones are adhered together, either with an adhesive or by heat sealing, such a seal being shown in the drawings at 52.

Referring now to FIG. 2, the tampon 11 is unwrapped by simply lifting and gripping the tab 20 and pulling it around the tampon's circumference. Because of the seal 52, adhering both perforated zones together, the forces exerted by pulling tab 20 will break all of the perforation in both zones and the two layers of wrapping will come off together. Only minor portions of the wrapper remain after the perforations are broken, i.e., end caps 54 and 56. These are easily removed because the minor area of contact that they make with the tampon offers little frictional resistance to removal.

FIG. 6 illustrates a portion of the first part of the wrapper to be removed from the tampon, with portions of zone 36 and zone 42 illustrated. It should be noted that the seal 52, sealing the apex areas of the two superimposed perforated zones extends beyond the perforation 50 which defines the apex of zone 42. This feature is useful in insuring that upon lifting the tab 20, a controlled tear will be propagated along the legs of zone 42. Specifically, it is advantageous that the first force applied to the apex area of zone 42 be applied at the narrowest portion of this area, i.e., immediately at perforation 50. Should such a force be applied at a wider portion of the apex area of zone 42, more force will be required to break the perforations and it is possible that the tear will sever the apex area and leave a substantial portion of wrapper remaining about the tampon. By extending the seal 52 beyond the perforation 50, it is assured that the initial force applied to tab 20 will peel open the seal in the extended area 52' and that thereafter the first force applied to zone 42 will occur exactly at perforation 50.

Referring now to FIG. 4, illustrated therein is an enlarged view of a portion of the wrapper showing the method by which a tear is made to propagate from one perforation to the next. As force is applied to tab 20, a tear 58 first develops. It has been discovered that, particularly with an unoriented film such as cellophane, this tear 58, rather than propagating longitudinally with respect to the wrapper, will tend to neck in toward the center of the wrapper. It is therefore important that the tear 58 intersects a perforation 24, the perforation "redirect" the tear both forwardly toward the opposite transverse edge 30 of the wrapper and also away from the center of the wrapper. To accomplish this, each of the perforations are set to form an acute angle (illustrated by the dimension A) between the longitudinal centerline of the wrapper and the perforations. Preferably such an angle should be at least about 40 degrees and no greater than about 75 degrees. It will be understood that this angle can be modified by varying the length of the perforations and the distance between them. However, because it is desirable to limit the perforation length (and hence reduce any chance of contaminating the product or significantly reducing the strength of the wrapper) the perforation generally should be no longer than about ¼ inch. Preferably the perforations in the portions 38', 40', 44' and 46' should be no longer than about ⅛ inch and the perforations in portions 38", 40", 44" and 46" should not be longer than about 1/16 inch. Within this range, an angle A of 55 to about 65 degrees is best suited.

Angle B, illustrated in FIG. 4, is the acute angle between the longitudinal center line of the wrapper and the locus line of center points of each of the perforations in the portion 38' of the perforated leg 38 angled toward the apex of the chevron. It is desirable to have this angle be as large as possible in that the larger this angle is, the smaller the area 60. Area 60 represents that portion of the wrapper which is not removed by breaking the perforations, i.e., that portion which remains as caps 56 and 54. On the other hand, when employing a material which tends to neck in upon tearing (such as cellophane), a larger angle B necessitates a longer length for each perforation and a greater angle A (and/or a closer distance between perforations) to insure that the tears propagate from one perforation to the next. Accordingly, it has been found that a suitable value for angle B is about 30° to about 60 degrees and preferably about 45 degrees.

It will be understood by those skilled in the art that the above discussions in connection with FIG. 4 applies to the configuration of the other corresponding parts of the perforation patterns of the wrapper of this invention.

What is claimed is:

1. A wrapped cylindrical body having a protective tearable wrapper and comprising:
   a cylindrical body;
   a generally rectangular wrapper having first and second transverse edges of a width equal to at least the axial length of the body and having first and second longitudinal edges of a length equal to at least twice the radial circumference of the body, said wrapper being rolled about the body;
   said wrapper being provided with a first pattern of perforations defining a first perforated zone and consisting of two legs, each beginning at the first transverse edge of said wrapper and extending toward and along each of the longitudinal edges of said wrapper;
   said wrapper being provided with a second pattern of perforations defining a second perforated zone and consisting of two legs, each beginning at a longitudinal distance from said first transverse edge of said wrapper equal to at least one radial circumference of said cylindrical body and extending generally parallel to each of the legs of said first pattern, said legs of said second pattern being displaced a distance inward of the legs of the first pattern, with respect to the longitudinal edges of said wrapper;
   said wrapper being rolled about said cylindrical body with the first perforated zone overlying the second perforated zone and adhered thereto at the first transverse edge;
   whereby, the perforations forming the two patterns are in misalignment and thereby prevent an open path to the cylindrical body and the body may be unwrapped by gripping the first transverse edge, the wrapper tearing along the two perforated patterns.

2. The wrapped cylindrical body of claim 1 wherein said perforations are slits cut into the wrapper and are set to form an acute angle between the longitudinal centerline of the wrapper and the perforations equal to at least 40° and no greater than about 75°.

3. The wrapped cylindrical body of claim 1 wherein said legs of said second pattern are displaced inward of the legs of said first pattern by a distance equal to at least 0.643 and less than 1.93 times the length of each of said perforations.

4. The wrapped cylindrical body of claim 1 wherein said perforations are between 1/16 and ¼ inches long.

5. The wrapped cylindrical body of claim 1 wherein said first transverse edge includes a tab for initiating the unwrapping.

6. The wrapped cylindrical body of claim 5 wherein said first transverse edge is sealed to the wrapper at points on either side of said tab.

7. The wrapped cylindrical body of claim 1 wherein said wrapper comprises cellophane.

8. A wrapped cylindrical body having a protective tearable wrapper comprising:
a cylindrical body;
a generally rectangular wrapper having first and second transverse edges of a width equal to at least the length of the body and having first and second longitudinal edges of a length equal to at least twice the radial circumference of the body and being rolled about the body;
said wrapper being provided with perforations forming first and second chevron patterns;
each of said chevrons having an apex approximately centrally positioned with respect to the transverse direction of the wrapper and two parallel legs extending in a direction from the first transverse edge to the second transverse edge and parallel to the longitudinal edges of the wrapper;
each of said chevrons having angular legs connecting said parallel legs to said apex;
the apex of said first chevron lying essentially within the first transverse edges of said wrapper and the apex of said second chevron being displaced from the first chevron apex a longitudinal distance equal to at least one circumference of said cylindrical body;
the parallel legs of second chevron being parallel to the parallel legs of said chevron and displaced a distance inward therefrom, with respect to the longitudinal edges of said wrapper;
said wrapper being rolled about said cylindrical body with the apex area of said first chevron overlying the apex area of the second chevron and having said areas adhered to one another;
whereby, in a wrapped condition, the perforations forming the chevron patterns are in misalignment and thereby prevent an open path to the cylindrical body and the body may be unwrapped by gripping the apex of the first chevron pattern at the first transverse edge of said wrapper, the wrapper tearing along the two perforated chevron patterns.

9. The wrapped cylindrical body of claim 8 wherein the apex areas of the two chevron patterns are adhered together by a seal that begins on the apex area of the second chevron and extends longitudinally toward the first transverse edge of the wrapper and beyond the apex of the second chevron pattern.

10. The wrapped cylindrical body of claim 8 wherein said perforations are slits cut into the wrapper and are set to form an acute angle between the longitudinal centerline of the wrapper and the perforations equal to at least about 40° and no greater than about 75°.

11. The wrapped cylindrical body of claim 8 wherein said legs of said second chevron are displaced inward of the legs of said first pattern by a distance equal to at least 0.64 and less than 1.93 times the length of each of said perforations.

12. The wrapped cylindrical body of claim 8 wherein said perforations are between 1/16 and ¼ inch long.

13. The wrapped cylindrical body of claim 8 wherein said first transverse edge includes, at the apex of said first chevron, a tab for initiating the unwrapping.

14. The wrapped cylindrical body of claim 13 wherein said first transverse edge is sealed to the wrapper at points on either side of said tab.

15. The wrapped cylindrical body of claim 8 wherein said angular legs of said chevrons each form an acute angle with the longitudinal centerline of said wrapper equal to at least about 30° and less than about 60°.

16. The wrapped cylindrical body of claim 8 wherein said wrapper comprises cellophane.

* * * * *

UNITED STATES PATENT AND TRADEMARK OFFICE
CERTIFICATE OF CORRECTION

PATENT NO. : 4,170,305
DATED : October 9, 1979
INVENTOR(S) : Raymond J. Hull, Jr. and William F. Hoppes It is certified that error appears in the above-identified patent and that said Letters Patent are hereby corrected as shown below:

In Column 8, line 4, "said chevron" should read -- said first chevron --.

Signed and Sealed this

Twenty-sixth Day of February 1980

[SEAL]

Attest:

SIDNEY A. DIAMOND

Attesting Officer

Commissioner of Patents and Trademarks